United States Patent [19]

Weeks et al.

[11] 4,006,061
[45] Feb. 1, 1977

[54] LACTATE DEHYDROGENASE DETERMINATION METHOD

[75] Inventors: Lloyd E. Weeks, St. Louis; John H. Johnson, Kirkwood, both of Mo.

[73] Assignee: Monsanto Company, St. Louis, Mo.

[22] Filed: Dec. 29, 1975

[21] Appl. No.: 644,799

[52] U.S. Cl. .................... 195/103.5 R; 204/195 B
[51] Int. Cl.$^2$ ........................................ C12K 1/04
[58] Field of Search ............ 195/103.5 R; 204/1 E, 204/195 B

[56] References Cited

UNITED STATES PATENTS

| | | | |
|---|---|---|---|
| 3,413,198 | 11/1968 | Deutsch | 195/103.5 R |
| 3,732,147 | 5/1973 | Fosker et al. | 195/103.5 R |
| 3,791,931 | 2/1974 | Thum et al. | 195/103.5 R |

OTHER PUBLICATIONS

Ells, "A Colorimetric Method for the Assay of Soluble Succinic Dehydrogenase and Pridinenucleotide-Linked Dehydrogenase," Archives of Biochem. & Biophy. vol. 85, pp. 561–562, (1959).
Amador et al., "Serum Lactic Dehydrogenase Activity: An Analytical Assessment of Current Assays," Clin. Chem., vol. 9, 1963, pp. 391–399.
Greenbaum et al., "The Estimation of the Oxidized and Reduced Forms of the Nicotinamide Nucleotides," Biochem. J., vol. 95, (1965), pp. 161–166.
Olson, "Differential Amperometric Measurement of Serum Lactate Dehydrogenase Activity Using Bindschedler's Green," Analytical Chem., vol. 46, No. 11, pp. 1544–1547, (1974).

*Primary Examiner*—A. Louis Monacell
*Assistant Examiner*—C. A. Fan
*Attorney, Agent, or Firm*—John D. Upham; Scott J. Meyer

[57] ABSTRACT

A method of determining lactate dehydrogenase activity in biological fluids comprising reacting a biological fluid sample with a coupled enzyme series in an oxygenated aqueous solution containing lactate, nicotinamide adenine dinucleotide and an electron transfer agent, and measuring the uptake of oxygen by the oxidation of the resulting NADH with an oxygen-sensing electrode.

7 Claims, No Drawings

LACTATE DEHYDROGENASE DETERMINATION METHOD

BACKGROUND OF THE INVENTION

This invention relates to a method for the determination of lactate and lactate dehydrogenase.

Lactate dehydrogenase (LDH) is a dehydrogenase enzyme which catalyzes the oxidation of L-lactate to pyruvate through a nicotinamide adenine dinucleotide (NAD) coupled enzyme reaction as follows:

lactate + NAD+ 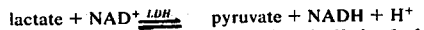 pyruvate + NADH + H+

The determination of LDH is of clinical significance in the diagnosis of various diseases. Thus, an elevated level of LDH is indicative of a myocardial infarction. Elevations of serum LDH are also observed in liver disease and in patients with certain types of carcinomas.

Numerous methods have been developed heretofore for the determination of LDH, including a variety of optical tests based on either the forward or reverse of the foregoing reaction, namely the oxidation of lactate to pyruvate or the reduction of pyruvate to lactate. The pH optimum of the forward reaction is 8.8 to 9.8, whereas for the reverse reaction it is 7.4 to 7.9. In the forward reaction the rate of increase, and in the reverse reaction the rate of decrease, in absorbance at 340 nm serves as the parameter of the enzyme activity in various spectrophotometric determination methods. The method which employs the forward reaction has been recommended as providing greater stability. N. Eng. J. Med. 261, 1259–66 (1959) and Clin. Chem. 9, 391–9 (1963).

Several colorimetric methods for the determination of LDH also are based on the foregoing coupled enzyme reaction. In one method, the pyruvate is reacted with 2,4-dinitrophenylhydrazine in a terminal indicator reaction to form the characteristic brown color of the corresponding 2,4-dinitrophenylhydrazone pyruvate which is measured colorimetrically at 440 nm.

In another colorimetric procedure, a terminal acceptor dye which gives the color change and an intermediary electron transfer agent to transfer hydrogen from the substrate to NAD are both employed. Thus, a phenazine methosulfate carrier has been used to couple the electron transfer between NADH and the terminal acceptor dye 2,6-dichlorophenol-indolphenol as described by Ells, Arch. Biochem. Biophys. 85, 561–62 (1959). Meldola blue is another typical electron carrier used heretofor in a similar such colorimetric determination of LDH as can be seen from U.S. Pat. No. 3,732,147.

While the foregoing optical methods for the determination of LDH are useful, they have the disadvantage in that each individual serum sample assay takes at least about 5 to 10 minutes to complete.

BRIEF SUMMARY OF THE INVENTION

In accordance with the present invention, a method is provided for the determination of lactate or LDH in biological fluids with an oxygen-sensing electrode system. This method employs the foregoing coupled enzyme reaction in which LDH catalyzes the oxidation of lactate to pyruvate in the presence of the coenzyme NAD. The resulting NADH is then oxidized in the presence of an electron transfer agent and the uptake of dissolved oxygen is determined with an oxygen-sensing electrode. This method advantageously can be carried out rapidly in less than about two minutes per sample assay.

DETAILED DESCRIPTION OF THE INVENTION

In general, the coupled enzyme system of the present invention proceeds initially according to the reaction sequence described above which leads to the production of the reduced coenzyme NADH. Instead of stopping at this point, the reaction sequence then continues further to the oxidation of NADH as follows:

lactate + NAD+ 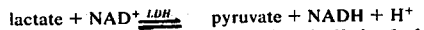 pyruvate + NADH + H+

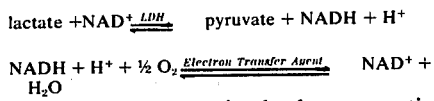

The uptake of oxygen in the latter reaction step is determined by an oxygen-sensing electrode. The rate of change in the electrode output is proportional to the lactate concentration or the LDH activity in the biological sample being tested, depending upon which of these two components is made the rate limiting factor in the reaction by employing an excess of the other. Thus, LDH activity is determined by employing an excess of lactate relative to the LDH activity in the biological sample; and lactate is determined by employing, conversely, an excess of LDH relative to the lactate concentration in the sample.

In order to provide for the desired conversion of lactate to pyruvate, the reaction is carried out under alkaline conditions ranging from a pH of about 8.8 to about 9.8 and preferably about 9.5 This pH range can be maintained by use of a suitable aqueous buffer, for example, conventional borate or pyrophosphate buffers.

Although an excess of NAD also will facilitate the desired forward reaction, the NADH being produced is immediately converted back to the NAD. Therefore, only a threshold amount of NAD need be employed, generally less than a molar equivalent amount.

The oxidation reaction in which the reduced form of the coenzyme, NADH, is converted to the oxidized form, NAD, requires the presence of an electron transfer agent or electron acceptor. Useful electron transfer agents include, for example, methylene blue, meldola blue, and phenazine methosulfate. Of these, phenazine methosulfate is preferred insofar as it produces a linear response over a more extended range of NADH concentration. Use of phenazine methosulfate electron transfer agent in the estimation of the oxidized and reduced forms of nicotinamide nucleotides with an oxygen-sensing electrode is described by Greenbaum et al, Biochem J. 95, 161–66 (1965).

The oxygen required for the foregoing oxidation reaction can be conveniently provided by saturating the reagent solution with air or oxygen.

Incubation time and temperature conditions employed in the coupled enzyme system are not critical and can be varied to facilitate completion of the reaction. Usually, the end point is reached in less than about 2 minutes at incubation temperatures ranging from about 25° to 40° C.

The coupled enzyme reaction series is conveniently carried out in a cuvette or other such sample container with an attached oxygen electrode. An attached recorder for the electrode indicates the electrode output. The reaction equilibrium point at which the reaction reaches a maximum as indicated by the output in millivolts on the recorder trace is taken as the end point for the determination.

In general, the oxygen-sensing electrode employed in this invention comprises an anode, a cathode, an electrolyte solution and means whereby the diffusion flow of oxygen through a semi-permeable membrane into the electrolyte is measured. The current output is a linear function of oxygen tension which is turn varies directly with the diffusion flow of oxygen.

Oxygen-sensing electrodes are well-known. The Clark $pO_2$ electrode described in U.S. Pat. No. 2,913,386 is typical. In this electrode, oxygen diffuses through a gas-permeable polymeric membrane and is reduced at a platinum cathode which is kept at a fixed potential with respect to a silver-silver chloride reference anode. Such electrodes have been used heretofore for the determination of blood glucose levels by measuring the oxygen uptake in a glucose oxidase enzyme catalyzed reaction. Illustrative of such use of the Clark $pO_2$ electrode are the report by Kunz and Stastny, Clin. Chem. 20, 1018–22 (1974) and the review article by Gough and Andrade, Science, 180, 380–84 (1973).

Oxygen-sensing electrodes also are commercially available or can be prepared in the laboratory. One such suitable electrode, commercially available from Beckman Instruments, Inc., consists of a gold cathode which is separated by an epoxy coating from a tubular silver anode. An inner sensor body is housed in a plastic casing and comes into contact with the sample reagent solution only through a Teflon (duPont polytetrafluoroethylene) plastic membrane. As oxygen diffuses through this membrane, it is electrochemically reduced at the cathode by an applied potential of 0.8 volts. The reaction causes a current to flow between the anode and cathode which is proportional to the partial pressure of oxygen in the reagent sample.

An example of a suitable laboratory prepared oxygensensing electrode for measuring dissolved oxygen in solution is described by Johnson et al., Biotechnol. J Bioeng. 6, 457–68 (1964). This electrode has a silver cathode, a lead anode, an acetate buffer as an electrolyte, and a Teflon plastic membrane. The electrolyte is an aqueous solution containing 0.1 molar sodium acetate and 0.1 molar acetic acid, or a more concentrated solution containing 5 M acetic acid and 0.5 M sodium acetate. A modification of this electrode is described by Borkowski and Johnson, Biotechnol. J Bioeng. 9, 635–39 (1967), in which the electrolyte is an aqueous solution of 5 M acetic acid, 0.5 M sodium acetate, 0.1 M lead acetate and has a pH of about 3. In addition, a silicone rubber insulated filter of glass wool or nylon is inserted between the lead anode and silver cathode to prevent lead particles from dropping onto the silver cathode and eventually causing a short circuit. The electrode has a linear response from below 0.00002 to over 0.2 atmosphere of oxygen. In this electrode, the reaction at the silver cathode is believed to be $$\tfrac{1}{2} O_2 + H_2O + 2e^- \rightarrow 2OH^-$$

while at the lead anode the loss of electrons produces lead ions.

$$Pb \rightarrow Pb^{++} + 2e^-$$

The lead ions combine with the hydroxyl to form lead hydroxide on the anode surface to result in an overall reaction as follows:

$$\tfrac{1}{2} O_2 + Pb + H_2O \rightarrow Pb(OH)_2$$

With acetate as the electrolyte, a deposit of basic lead acetate builds up on the lead surface and lead salts accumulate in the electrolyte. The expendable materials thereby are the lead anode and the acetate of the electrolyte.

A further modification of the above-described Johnson electrode is disclosed by Elsworth, The Chemical Engineer, February 1972, pp. 63–71.

Still other oxygen-sensing electrodes for use in the present invention are described in U.S. Pat. Nos. 3,449,231, 3,454,485 and 3,539,455.

Although Teflon plastic and silicone rubber have been specifically described above, it should be understood that other membrane materials permeable to oxygen and impermeable to water and electrolytes can be used in the oxygen-sensing electrode, for example, polyethylene, polypropylene, polystyrene and polyvinyl chloride. Other suitable anode-cathode materials include, for example, any noble metal cathode such as gold, silver or rhodium in conjunction with a zinc, cadmium or lead anode.

In the instant invention, the diffusion flow of oxygen through the plastic membrane is reduced by the presence of LDH in the coupled enzyme catalyzed reaction as defined hereinbefore.

The following detailed examples will further illustrate the invention although it should be understood that the invention is not limited to these specific examples.

EXAMPLE 1

A buffer-lactate solution was prepared by forming an aqueous solution of 0.05 molar $Na_4P_2O_7$ and 0.078 molar lactic acid and adjusting to pH 9.5. This solution was deaerated under vacuum and then reaerated to saturation while stirring at 37° C for 30 minutes. One ml of the buffer-lactate solution was pumped into a cuvette with an attached oxygen-sensing electrode while stirring at 250 rpm. This was followed by the addition of 50 microliters of NAD (10 mg./ml.), 50 microliters of phenazine methosulfate (1 mg/ml), and 100 microliters of a standard serum sample to be assayed for LDH activity. The maximum rate of decrease in electrode output in millivolts/minute was determined from the recorder trace. This decrease occurred within about one minute following an initial 5 to 20 second lag. Six serum samples for use in this assay were prepared to contain 0%, 20%, 40%, 60%, 80%, and 100%, respectively, of Stattrol (Worthington Biochemical Corporation reference standard reported to contain 344±25 I.U. of LDH per liter) and a complement of Difco TC Human Serum Desiccated, reconstituted for use and reported to contain virtually no LDH activity. The relationship of LDH activity in the thus prepared standard serum samples vs. mv/min electrode output was found to be substantially linear.

The oxygen-sensing electrode employed employed in this example was a modification of the membrane electrode described by Elsworth, The Chemical Engineer, February 1972, pp. 63–71. This modification employed a silver cathode and a lead anode. The electrolyte, which consisted of 5.0M acetic acid, 0.5M sodium acetate and 0.1M lead acetate, instead of being used in a liquid phase as described by Elsworth, was employed in a gelled form by the addition of a small amount of Syton (Monsanto silica gel) and then applied in film form covered by a Teflon plastic film.

The electrode was attached to a cuvette, which had an inner Teflon plastic sleeve lining, by entry from the side of the cuvette. The reagents were introduced into the cuvette by entry from the open top. An agitated water bath assembly was employed to maintain a stirring speed of about 250 rpm and a temperature of about 37° C for the reaction components. A Beckman recorder attached to the electrode terminals indicated the electrode output.

EXAMPLE 2

Example 1 is repeated except that meldola blue is used in place of the phenazine methosulfate. Substantially similar results are obtained but with slightly less efficiency and linearity than obtained by the use of phenazine methosulfate.

Various other examples will be apparent to the person skilled in the art after reading the foregoing disclosure without departing from the spirit and scope of the invention and it is intended that all such examples be included within the scope of the appended claims.

What is claimed is:

1. The method of determining lactate dehydrogenase activity in a biological fluid comprising reacting said biological fluid with an aqueous solution saturated with air or oxygen and containing lactate, NAD and an electron acceptor at a temperature of from about 25° to about 40° C and a pH of from about 8.8 to about 9.8 and measuring the uptake of oxygen by the oxidation of the resulting NADH with an oxygen-sensing electrode.

2. The method of claim 1 in which the biological fluid is blood serum or plasma.

3. The method of claim 1 in which the electron acceptor is phenazine methosulfate.

4. The method of claim 1 in which the electron acceptor is meldola blue.

5. The method of claim 3 in which the biological fluid is blood plasma or serum.

6. The method of claim 4 in which the biological fluid is blood plasma or serum.

7. The method of determining lactate activity in a biological fluid comprising reacting said biological fluid with an aqueous solution saturated with air or oxygen and containing lactate dehydrogenase, NAD and an electron acceptor at a temperature of from about 25° to about 40° C and a pH of from about 8.8 to about 9.8 and measuring the uptake of oxygen by the oxidation of the resulting NADH with an oxygen-sensing electrode.

* * * * *